United States Patent
Potter

(10) Patent No.: US 6,696,409 B1
(45) Date of Patent: Feb. 24, 2004

(54) NEUROPEPTIDE Y AGONISTS

(75) Inventor: Erica Potter, Randwick (AU)

(73) Assignee: Prince of Wales Medical Research Institute Limited (POWMR Ltd.), Randwick (AU)

( * ) Notice: Subject to any disclaimer, the term of this patent is extended or adjusted under 35 U.S.C. 154(b) by 0 days.

(21) Appl. No.: 09/641,567

(22) Filed: Aug. 18, 2000

Related U.S. Application Data

(63) Continuation of application No. 09/456,837, filed on Dec. 7, 1999, now abandoned, which is a continuation of application No. 09/194,871, filed as application No. PCT/AU97/00352 on Jun. 5, 1997, now abandoned.

(30) Foreign Application Priority Data

Jun. 5, 1996 (AU) .......................................... PO 0290

(51) Int. Cl.$^7$ .................. A61K 38/00; A61K 38/28; C07K 7/00; C07K 5/00
(52) U.S. Cl. ................. 514/2; 514/4; 514/11; 514/12; 530/300; 530/317; 530/321; 530/324
(58) Field of Search ............. 514/2, 4, 11, 12; 530/300, 317, 321, 324

(56) References Cited

U.S. PATENT DOCUMENTS 5,696,093 A * 12/1997 Tseng et al. .................. 514/14
5,972,888 A * 10/1999 Bue-Vallesket et al. ....... 514/12

FOREIGN PATENT DOCUMENTS

| DE | 3811 193 A1 | 10/1989 |
| WO | WO 94/22467 | 10/1999 |

OTHER PUBLICATIONS

Reymond et al. (1992) "Truncated, Branched, and/or Cyclic Analogs of Neuropeptide Y: Importance of the Pancreatic Peptide Fold in the Design of Specific Y2 Receptor Ligands." J. Med. Chem 35:3653–3659.*

Biopolymers, 1991, 31, 613–619(Jung, G et al) "α–Helical small molecular size analogues of neuropeptide Y: structure–activity relationships".

Br. J. Pharmacol., 1994, 111, 1129–1134 (Kahl, U et al) "Functional effects and ligand binding of chimeric galanin–neuropeptide Y (NPY) peptides on NPY and galanin receptor types."

Eur. J. Pharmacol., Mol. Pharmacol Sect, 1994, 267, 253–262 (Potter, E K et al) "A novel neuropeptide Y analogue, N–acetyl[Leu$^{26}$, Leu$^{31}$]neuropeptide Y–(24–36). . ".

Eur. J Pharmacol., 1992, 232, 271–278 (Grundemar, L et al). "Activation of neuropeptide $Y_1$ and neuropeptide $Y_2$ receptors by substituted and truncated neuropeptide Y analogues. . . ".

Peptide Res., 1991, 4, 88–94 (Beck–Sickinger, A G et al) "Semiautomated T–bag peptide synthesis using 9–fluorenylmethoxycarbonyl strategy and. . . .".

Int. J Peptide Protein Res., 1990, 36, 522–530 (Beck–Sickinger, A G et al) "Neuropeptide Y: identification of the binding site."

* cited by examiner

Primary Examiner—Gary Kunz
Assistant Examiner—Christopher James Nichols
(74) Attorney, Agent, or Firm—Nixon & Vanderhye

(57) ABSTRACT

A ligand for a neuropeptide Y receptor which has the formula:

Ac-Ala-Arg-Ala-Ala-Leu-Asn-Ala-Ala-Thr-Arg-Gln-Arg-Tyr-NH$_2$ (SEQ ID NO:1), or

Ac-Ala-Arg-His-Tyr-Leu-Asn-Leu-Leu-Thr-Arg-Gln-Arg-Tyr-NH$_2$ (SEQ ID NO:2), or

Ac-Leu-Ala-His-Tyr-Leu-Asn-Leu-Leu-Thr-Arg-Gln-Arg-Tyr-NH$_2$ (SEQ ID NO:3), or

Ac-Leu-Arg-Ala-Tyr-Leu-Asn-Leu-Leu-Thr-Arg-Gln-Arg-Tyr-NH$_2$ (SEQ ID NO:4), or

Ac-Leu-Arg-His-Ala-Leu-Asn-Leu-Leu-Thr-Arg-Gln-Arg-Tyr-NH$_2$, (SEQ ID NO:5), or

Ac-Leu-Arg-His-Tyr-Ala-Asn-Leu-Leu-Thr-Arg-Gln-Arg-Tyr-NH$_2$(SEQ ID NO:6), or

Ac-Leu-Arg-His-Tyr-Leu-Ala-Leu-Leu-Thr-Arg-Gln-Arg-Tyr-NH$_2$, (SEQ ID NO:7), or

Ac-Leu-Arg-His-Tyr-Leu-Asn-Ala-Leu-Thr-Arg-Gln-Arg-Tyr-NH$_2$, (SEQ ID NO:8), or

Ac-Leu-Arg-His-Tyr-Leu-Asn-Leu-Ala-Thr-Arg-Gln-Arg-Tyr-NH$_2$, (SEQ ID NO:9), or

Ac-Ala-Arg-His-Ala-Leu-Asn-Leu-Leu-Thr-Arg-Gln-Arg-Tyr-NH$_2$, (SEQ ID NO:10), or

Ac-Leu-Arg-Ala-Ala-Leu-Asn-Leu-Leu-Thr-Arg-Gln-Arg-Tyr-NH$_2$, (SEQ ID NO:11), wherein Ac is acetyl.

4 Claims, 1 Drawing Sheet

SEQUENCE LISTING

<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ala Arg Ala Ala Leu Asn Ala Ala Thr Arg Gln Arg Tyr
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Arg His Tyr Leu Asn Leu Leu Thr Arg Gln Arg Tyr
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ala His Tyr Leu Asn Leu Leu Thr Arg Gln Arg Tyr
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Arg Ala Tyr Leu Asn Leu Leu Thr Arg Gln Arg Tyr
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Arg His Ala Leu Asn Leu Leu Thr Arg Gln Arg Tyr
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Arg His Tyr Ala Asn Leu Leu Thr Arg Gln Arg Tyr
 1               5                  10

<210> SEQ ID NO 7
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Arg His Tyr Leu Ala Leu Leu Thr Arg Gln Arg Tyr
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Arg His Tyr Leu Asn Ala Leu Thr Arg Gln Arg Tyr
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Arg His Tyr Leu Asn Leu Ala Thr Arg Gln Arg Tyr
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Arg His Ala Leu Asn Leu Leu Thr Arg Gln Arg Tyr
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Arg Ala Ala Leu Asn Leu Leu Thr Arg Gln Arg Tyr
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Arg His Tyr Leu Asn Ala Ala Thr Arg Gln Arg Tyr
```

```
                         -continued
   1             5              10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg Ala Ala Leu Asn Ala Ala Thr Arg Gln Arg Phe
  1               5                  10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Ala Ala Leu Gln Ile Leu Ser Arg Asn Arg Tyr
  1               5                  10
```

NEUROPEPTIDE Y AGONISTS

"This application is a CON of Ser. No. 09/456,837 filed Dec. 7, 1999, now abandoned, which is a CON of 09/194,871 filed Dec. 4, 1998, now abandoned, which is a §371 of PCT/AU97/00352 filed Jun. 5, 1997, which claims priority to AUSTRALIA PO 0290 filed Jun. 5, 1996."

FIELD OF INVENTION

The present invention relates to peptides which mimic certain of the biological activities of Neuropeptide Tyrosine (NPY) at specific NPY receptors that modulate neuronal release of physiologically active substances. These receptors are often located on neurones at neuroeffector junctions and, in some tissues and species, have been classified as of the NPY Y2 receptor subtype. In addition, the present invention relates to pharmaceutical compositions including, as the active ingredient, these peptides and to methods of treatment involving the administration of these compositions.

BACKGROUND OF INVENTION

Neuropeptide Y, a 36 amino acid peptide belonging to the pancreatic polypeptide family, was first isolated from porcine brain in 1982 (Tatemoto et al., 1982) and has since been identified in most sympathetic postganglionic neurons innervating the cardiovascular system, where it is co-localised with noradrenaline (Potter, 1988). In the cardiovascular system it raises blood pressure by an action on postjunctional neuropeptide Y receptors (Dahlöf et al., 1985; Potter, 1985; Revington et al., 1987; Potter and McCloskey, 1992) and inhibits neurotransmitter release—both acetylcholine (Revington et al., 1987; Warner and Levy, 1989) and noradrenaline (Edvinsson, 1988)—by acting on prejunctional neuropeptide Y receptors. Receptors for neuropeptide Y are also located on sensory nerve terminals and their activation can modulate local neurogenic responses (Grundemar et al., 1990;1993). These two receptor subtypes have been called neuropeptide Y $Y_1$(postjunctional) and neuropeptide Y Y2 (prejunctional) on the basis of the different responses to a truncated analog of the related peptide YY-(13–36), when compared with neuropeptide Y in in vitro assay systems (Wahlestedt et al., 1986). Apart from these historically well-defined neuropeptide Y receptors the existence of a number of other subtypes (Y3, Y4, Y5, Y6 and Y7) have been suggested on pharmacological grounds and details of the cloning of receptors corresponding to Y1, Y2, Y4 and Y5 have been published (Herzog et al., 1992; Gerald et al., 1995; Bard et al., 1995; Gerald et al., 1996). The distribution and physiological significance of these various receptor subtypes has yet to be defined. Although some controversy has existed about the selectivity of truncated forms of neuropeptide Y for one or other receptor subtype (Potter et al., 1989), the emerging picture supports the initial classification into pre- and postjunctional receptor subtypes. Cell lines have been developed which express one or other neuropeptide Y receptor subtype and the development of receptor-selective analogs of neuropeptide Y has focussed mainly on binding characteristics in these cell lines (Sheikh et al., 1989; Aakerlund et al., 1990; Fuhlendorff et al., 1990). More recently, a cDNA encoding the neuropeptide Y $Y_1$ receptor has been cloned and cell lines expressing the cloned receptor have been analysed for both specific binding of neuropeptide Y analogs (Herzog et al., 1992) and functional responses elicited by specific analogs. From such binding studies, combined with subsequent studies in vivo, two analogs have been classified as acting specifically on the postjunctional (neuropeptide Y $Y_1$) receptor. These neuropeptide Y $Y_1$ selective analogs, ($Pro^{34}$) neuropeptide Y and ($Leu^{31}$, $Pro^{34}$) neuropeptide Y, mimic the action of neuropeptide Y in raising blood pressure, and also share similar binding to cell lines expressing only neuropeptide Y $Y_1$ receptors e.g. the human neuroblastoma cell line SK-N-MC and fibroblast lines expressing the cloned neuropeptide Y $Y_1$ receptor (Herzog et al., 1992). Neither exhibits the neuropeptide Y $Y_2$ receptor action of inhibiting cardiac vagal action in vivo, a manifestation of inhibition of acetylcholine release (Potter et al., 1991; Potter and McCloskey, 1992).

Activation of neuronal prejunctional NPY receptors generally inhibits nerve activity, reducing the release of neurotransmitters in response to nerve impulses and in response to local factors acting to release neurotransmitters (Wahlestedt et al., 1986).

NPY-containing neurons are evident in the nasal mucosa of various species including man, often associated with glandular acini and blood vessels (Baraniuk et. Al., 1990; Grunditz et. al., 1994). Stimulation of the parasympathetic nerve supply to the nasal mucosa (vidian nerve) in dogs increases blood flow in the region and the major part of this effect is atropine resistant. Intravenous administration of NPY reduces vasodilitation due to parasympathetic nerve stimulation, an effect that was not mimicked by the NPY Y1-selective agonist [Leu31, Pro34]NPY, but was mimicked by administration of the NPY Y2-receptor agonist N-acetyl [Leu28,Leu31]NPY(24–36) (Lacroix et al., 1994). This is consistent with a prejunctional NPY Y2-like receptor-mediated inhibition of transmitter release from parasympathetic nerve terminals.

The prejunctional or neuropeptide Y $Y_2$ receptor classification was based on actions of peptide YY (13–36) but in many systems this molecule, as well as neuropeptide Y-(13–36), does exhibit pressor activity (Rioux et al., 1986; Lundberg, et al., 1988; Potter et al., 1989). This has been interpreted by some to indicate that in some vascular beds there are two types of neuropeptide Y receptor (both neuropeptide Y $Y_1$ and neuropeptide Y $Y_2$) on postjunctional membranes (Schwartz et al., 1989). However the lack of selectivity of these molecules may be due to retention of partial agonist activity on $Y_1$ receptors, which permits them to evoke a reduced functional response. We have previously described a 13–36 analog of neuropeptide Y, ($Leu^{17}$, $Glu^{19}$, $Ala^{21}$, $Ala^{22}$, $Glu^{23}$, $Leu^{28}$, $Leu^{31}$) neuropeptide Y-(13–36) (ANA neuropeptide Y-(13–36)) which displayed prejunctional activity equivalent to the whole neuropeptide Y molecule in studies in vivo (Potter et al., 1989). However, this analog still retained significant pressor activity, or neuropeptide Y $Y_1$ receptor-mediated interactions.

We have also previously described analogs of neuropeptide Y which mimic the action of neuropeptide Y in inhibiting cardiac vagal action but have no pressor action. Consistent with these functional responses are binding studies with one analog, N-acetyl [$Leu^{28}$, $Leu^3$] neuropeptide Y-(24–36), which showed significant affinity for the neuropeptide Y $Y_2$ receptor subtype expressed on the human neuroblastoma cell line SMS-KAN, but no affinity for the neuropeptide Y $Y_1$ receptor type expressed on the human cell line SK-N-MC (Potter et al., 1994). In addition, this analog did not stimulate the human neuropeptide Y $Y_1$ receptor expressed in fibroblast cells to induce an increase in cytosolic calcium, although the receptor responds to intact neuropeptide Y.

DISCLOSURE OF INVENTION

The present inventors have now developed novel peptides that mimic responses attributed to activation of neuropeptide Y Y2-like receptors. In in vitro assays these agonists show high affinity at neuropeptide Y Y2 receptors and have low affinity for NPY Y1 receptors. In in vivo assays the new agonists exhibit similar or enhanced NPY Y2-receptor-like agonist activity when compared with N-acetyl [Leu$^{28}$, Leu$^{31}$] neuropeptide Y-(24–36) and they show no pressor or $Y_1$-receptor activiy at doses eliciting maximal neuropeptide Y Y2-like agonist action.

Accordingly, in the first aspect the present invention consists in a ligand for a neuropeptide Y receptor having the formula:

X1-X2-X3-X4-X5-X6-X7-X8-X9-X10-X11-X12-X13-X14-X15 wherein
- X1 is H, R1-CO or one or two naturally occurring amino acids
- X2 is Leu, Ile, Val, Nie, Sar, Gly, Ala, Aib, D-Leu, D-Ile, D-Val, D-Ala or D-Nle;
- X3 is Arg, Lys, Orn, Ala, Dbu or His;
- X4 is His, Lys, Arg, Ala, Gly, Ser, Thr, Asn, Gln or Aib;
- X5 is Tyr, Phe, Ala, Gly, Ser, Thr, Asn, Gln or Aib;
- X6 is Leu, Ile, Val, Ala, Arg or Nle;
- X7 is Asn, Ala or Gln;
- X8 is Leu, Ile, Val, Ala, Aib or Nle;
- X9 is Leu, Ile, Val, Ala, Aib or Nle;
- X10 is Thr, Ala or Ser;
- X11 is Arg, Lys or Orn;
- X12 is Gln, Pro or Asn;
- X13 is Arg, Lys or Orn;
- X14 is Tyr, Phe, His, Trp, D-Tyr, D-Phe, D-His or D-Trp;
- X15 is OH, $NH_2$, NHR2, NR3R4 or one or two naturally occurring amino acids with the terminal amino acid being in the normal or amide form;

wherein R1, R2, R3 and R4 are independently alkyl groups, straight, branched or alicyclic in structure; and
wherein at least one of X2 to X10 is Ala.

Abbreviations:
- Sar: Sarcosine or N-methylglycine
- Aib: Aminoisobutyric acid
- Orn: Ornithine
- Dbu: Diaminobutyric acid In a preferred embodiment, at least two groups selected from X2, X4, X5, X8 and X9 are Ala. In a particularly preferred embodiment, X2 and X5 are Ala.

In a further preferred embodiment, R1 is an alkyl group selected from methyl, ethyl, n-butyl, t-butyl, cyclohexyl and other alkyl groups with 10 or less carbon atoms.

In a further preferred embodiment, R2, R3 and R4 are alkyl groups selected independently from methyl, ethyl, isopropyl, n-butyl, cyclohexyl and other alkyl groups with 10 or less carbon atoms.

In a preferred embodiment of this invention the neuropeptide Y receptor is a neuropeptide Y Y2-like receptor. By "neuropeptide Y Y2-like receptor" we mean a receptor which shares pharmacological properties with the human neuropeptide Y Y2 receptor. Such receptors may modulate the release of neurotransmitters such as acetylcholine and noradrenaline and may modulate the release of effectors from sensory nerves. Some NPY receptor subtypes, for example Y5, can be activated by ligands with high potency at NPY Y2 receptors but low potency at NPY Y1 receptors (Gerald et al., 1996) and are therefore Y2-like. In a most preferred embodiment, the receptor is a neuropeptide Y Y2 receptor.

The ligands of the invention may be in multimeric form; ie. they may be in dimeric or trimeric form.

It will be appreciated by those skilled in the art that a number of modifications may also be made to the peptides of the present invention without deleteriously affecting the biological activity of the peptide. This may be achieved by various changes, such as insertions and substitutions, either conservative or non-conservative in the peptide sequence where such changes do not substantially decrease the biological activity of the peptide.

Modifications of the peptides contemplated herein include, but are not limited to, modifications to side chains, incorporation of unnatural amino acids and/or their derivatives during peptide synthesis and the use of crosslinkers and other methods which impose conformational constraints on the peptides.

Examples of side chain modifications contemplated by the present invention include modifications of amino groups such as by reductive alkylation by reaction with an aldehyde followed by reduction with $NaBH_4$; amidation with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with NaBH4.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Tryptophan residues may be modified by, for example, oxidation with N-bromosuccinimide or alkylation of the indole ring with 2-hydroxy-5-bitrobenzyl bromide or sulphenyl halides. Tyrosine residues on the other hand, may be altered by nitration with tetranitromethane to form 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid; 2-thienyl alanine and/or D-isomers of amino acids.

As a further example, it is possible in the present invention to replace the residue at X14 by other non-natural amino acids with hydrophobic side chains such as Cha (beta-cyclohexyl-L-alanine), Nal (beta-(2-naphthyl)-alanine), Phg (L-phenylglycine), Tic (L-1,2,3,4-tetrahydroisoquinoline 3-carboxylic acid), Thi (beta-(2-thienyl)-L-alanine), or their D-isomers, without substantially altering the biological activity.

It may also be possible to add various groups to the peptide of the present invention to confer advantages such as increased potency or extended half life in vivo without substantially decreasing the biological activity of the peptide. It is intended that such modifications to the peptide of the present invention which do not result in a decrease in biological activity are within the scope of the present invention.

The ligands of the present invention may be useful in treatment of the following conditions:

Conditions related to inflammation (such as nasal inflammation, rhinitis including allergic and vasomotor, asthma, arthritis).

Conditions related to neurogenic inflammation (such as migraine, headache, inflammation of the eye, rhinitis, etc.).

Rhinitis—vasomotor rhinitis.

Respiratory diseases (such as pulomonary congestion, asthma, upper respiratory tract inflammation).

Sleep disorders.

Conditions related to increased sympathetic nerve activity.

Disorders related to sexual dysfunction and reproductive disorders.

Disorders or diseases pertaining to the heart, blood vessels or the renal system (such as vasospasm, heart failure, shock, cardiac hypertrophy, increased blood pressure, angina, myocardial infarction, sudden cardiac death, arrhythmia, peripheral vascular disease, renal failure, etc.).

Conditions related to increased sympathetic nerve activity (e.g. during or after coronary artery surgery, and operations and surgery in the gastrointestinal tract).

Cerebral diseases and diseases related to pain or nociception.

Diseases related to the central nervous system (e.g. cerebral infarction, neurodegeneration, epilepsy, stroke, cerebral vasospasm, depression, anxiety or dementia).

Diseases related to abnormal gastrointestinal motility and secretion (e.g. Crohn's disease).

Diseases and conditions affecting the urinogenital system (e.g. urinary incontinence).

Abnormal drink and food intake disorders (such as obesity, anorexia, bulimia etc.).

In a second aspect, therefore, the present invention consists in a composition for use in relieving nasal congestion or treating vasoconstriction predisposing to acute renal failure, anti-hypertensive conditions, cardiovascular disorders, conditions related to pulmonary congestion, inflammation, neurogenic inflammation, sleep disorders, conditions related to increased sympathetic nerve activity, diseases related to the central nervous system, conditions related to pain or nociception, diseases related to gastrointestinal motility and secretion, obesity, or Alzheimer's disease, or as an anti-psychotic, the composition including the peptide of the first aspect of the present invention and a pharmaceutical carrier.

In a third aspect the present invention consists in a method of relieving nasal congestion, attenuating cardiac vagal action, treating vasoconstriction predisposing to acute renal failure, hypertension, cardiovascular disorders, conditions related to pulmonary congestion, inflammation, neurogenic inflamation, sleep disorders, conditions related to increased sympathetic nerve activity, diseases related to the central nervous system, conditions related to pain or nociception, diseases related to gastrointestinal motility and secretion, obesity, or Alzheimer's disease in a subject comprising administering to the subject an effective amount of the composition of the second aspect of the present invention.

In a preferred embodiment of the third aspect of the present invention the subject is suffering from nasal congestion, pulmonary congestion or vasoconstriction predisposing to acute renal failure. In a further preferred embodiment the composition is administered as a nasal spray.

The active compound may be administered in a convenient manner such as by the oral, intravenous (where water soluble), intramuscular, subcutaneous, intranasal, intradermal or suppository routes or implanting (eg using slow release molecules). It may also be inhaled (dry or in solution) into the lungs. Depending on the route of administration, the active ingredients may be required to be coated in a material to protect said ingredients from the action of enzymes, acids and other natural conditions which may inactivate said ingredients. For example, low lipophilicity of peptides might allow them to be destroyed in the gastrointestinal tract by enzymes capable of cleaving peptide bonds and in the stomach by acid hydrolysis. In order to administer peptides by other than parenteral administration, they could be coated by, or administered with, a material to prevent its inactivation. For example, peptides may be administered in a solvent, in liposomes, or co-administered with enzyme inhibitors. Enzyme inhibitors include pancreatic trypsin inhibitor, diisopropylfluorophosphate (DFP) and trasylol. Liposomes include water-in-oil emulsions as well as conventional liposomes.

The active compounds may also be administered parenterally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example glycerol, propylene glycol and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, sorbic acid, thiomersal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various other ingredients as required, followed by filtered sterilization. Generally, dispersions are prepared by incorporating the various sterilised ingredient into a sterile vehicle which contains the basic dispersion medium and the required other ingredients. In the case of sterile powders for use as such or for the preparation of sterile injectable solutions, the preferred methods of preparation are vacuum drying and the freeze-drying technique which yield a powder of the active ingredient plus any additional desired ingredient from previously sterile-filtered solution thereof.

BRIEF DESCRIPTION OF THE DRAWING

In order that the nature of the present invention may be more clearly understood, preferred forms thereof will now be described with reference to the following examples and Figure in which.

MATERIALS AND METHODS

In Vivo

Figure 1:
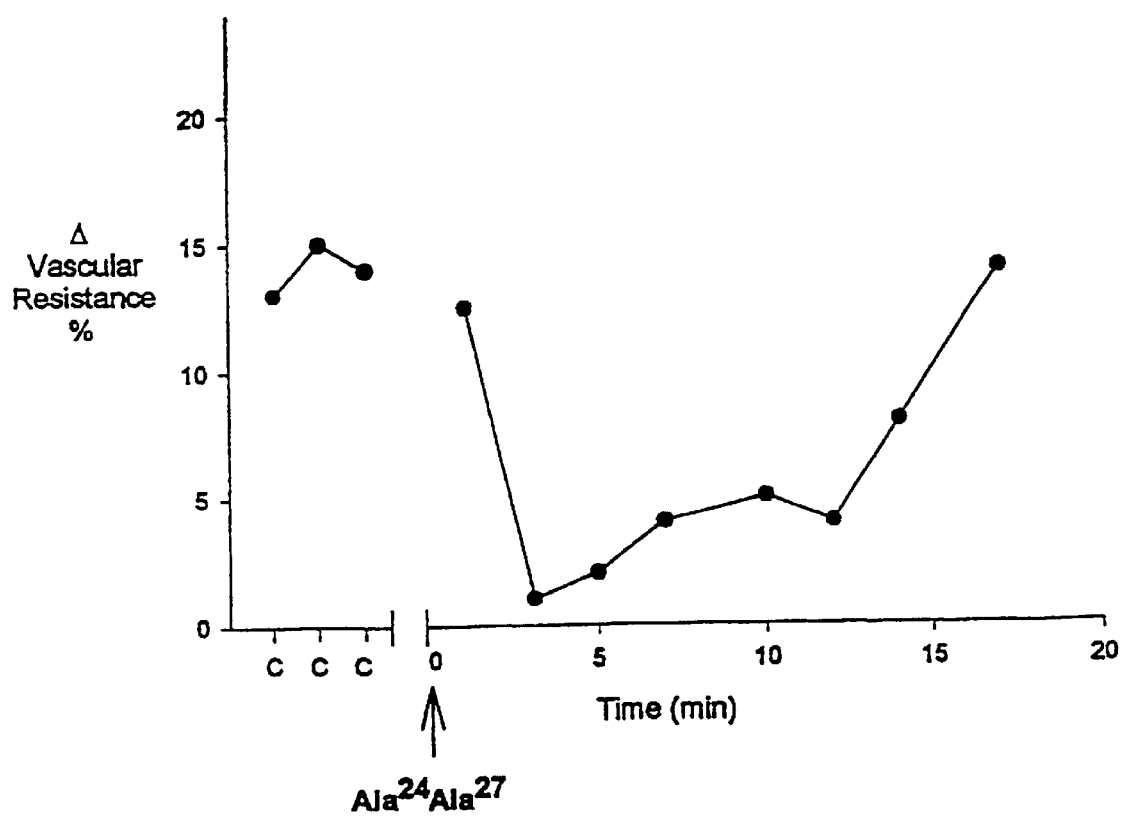
FIG. 1 shows the effect of Ac[Ala24, Ala27, Leu28, Leu31]NPY(24–36) on increased renal vascular resistance in rats elicited by electrical stimulation of the renal sympathetic nerve.

Experiments were carried out on adult rats (Wistar) of both sexes (250–350 g), anaesthetised with sodium pentobarbitone (Nembutal, Boehringer-Ingleheim; 60 mg/kg, i.p.). The trachea was cannulated and the animal artificially ventilated. The femoral vein was cannulated for administration of peptides and further doses of anaesthetic. The left femoral artery was cannulated to record arterial pressure. Both vagus nerves were cut. This was done to eliminate vagally-mediated reflex effects on the heart which can occur when blood pressure is raised by neuropeptide Y. The cardiac end of the right vagus nerve was stimulated every 30 s with a 6 s train of supramaximal stimuli (2 Hz, 1 ms; 7V) using an isolated, square-wave stimulator (Grass Instruments). The frequency was chosen to increase pulse interval by approximately 100 ms, a submaximal effect on this variable. The electrocardiogram was measured using needle electrodes and monitored on one channel of an osciloscope. Pulse interval (the period between successive beats of the heart) was recorded beat-by-beat by triggering from ECG. Pulse interval and arterial pressure were recorded on the pen recorder.

Dose-response curves were constructed from group data for all rats. Because of the long time-course of action of the peptides tested, not all peptides were given to each rat. Usually however, each rat received neuropeptide Y and two other peptides.

As an indication of prejunctional activity two parameters were measured; the maximum percent inhibition of the increase in pulse interval evoked by stimulation of the vagus nerve following injection of peptide and the time to half recovery of this effect (T50). For pressor action, an indicator of postjunctional activity, two parameters were also measured; the peak pressor response following injection of peptide and the duration of the increase in blood pressure. These indices give a reliable measure of the actions of a peptide at pre- and postjunctional sites, and have been used previously in this laboratory for this purpose; Potter et al., 1989; Potter et al., 1991). Results were analysed using a one-way ANOVA.

Methods for Experiments on Kidney Blood Flow (In Vivo).

Experiments were carried out in six, adult, mongrel dogs of both sexes weighing between 18 and 26 kg. The dogs were anaesthetised with a bolus injection of sodium pentobarbitone (36 mg/kg intravenous; Nembutal, Boehringer Ingelheim) and then maintained on an infusion (2–3 mg/kg/hr). The animal was artificially ventilated, maintained at constant temperature and blood pressure and heart rate were monitored continuously.

The left kidney was exposed retroperitoneally and renal arterial blood flow was monitored continuously (Pernow & Lundberg, 1989a), using a transonic flow probe (Transonic System Inc., N.Y.). Postganglionic nerves to the kidney were isolated, cut and placed over bipolar, platinum electrodes for stimulation (1–10 Hz, 5–10 V, 1–5 msec). Noradrenaline and neuropeptide Y have been shown to co-exist in the kidney and are released together on stimulation of the renal nerves (Pernow & Lundberg, 1989b).

The renal nerve was stimulated over a range of frequencies (1–10 Hz) for 30 secs and a frequency-response curve constructed. The responses were measured at the peak change in flow. These frequency-response relationships were examined before and after a bolus dose (40 nmol/kg) of the NPY Y2 receptor agonist. Responses were reported as change in vascular resistance.

Methods for Binding Experiments (In Vitro) Cell Culture

SK-N-MC cells expressing the human Y1 receptor and SMS-MSN cells expressing the human Y2 receptor were obtained from the ATCC. They were cultured in 1:1 DMEM: Ham's F12 medium (ICN) containing 10% fetal calf serum, 0.1% non-essential amino acids, 0.2 mM glutamine, and 0.056% sodium bicarbonate. Confluent cells were harvested in scraping and pellets were stored at −80° C. On the day of use cells were thawed, washed once in binding buffer salts, passed several times through a 22 ga. needle, and the protein content was assayed using bicinchoninic acid (BCA kit, Pierce). Cell volume was adjusted to give a protein concentration of 200–400 $\mu$g/ml (SMS-MSN cells) or 400–800 $\mu$g/ml (SK-N-MC cells), and BSA and protease inhibitors were added.

Receptor Binding Assays

Receptor binding assays were performed in Multiscreen FC plates (Millipore) [Gregor et al., 1996]., pre-coated overnight at 4° C. with 0.5% PVP/0.1% Tween-20 [Scott et al, 1995] to prevent non-specific binding. Just before use, plates were filtered and washed twice with 50 mM Tris-HCI pH 7.4/0.1% BSA. 30 pM [125I]NPY (Amersham), competitors (10 pM to 1 $\mu$M) and cells (10–20 $\mu$g for SMS-MSN or 20–40 $\mu$g for SK-N-MG) were incubated for 2.5 h at room temp in a total volume of 200 $\mu$l, in binding buffer containing 50 mM Tris-HCI pH 7.4, 115 mM NaCl, 15 mM KCl, 5 mM CaCl2, 2 mM MgSO4, 1.25 mM KH2PO4, 25 mM NaHCO3, 10 mM glucose, 0.1% BSA, 4 mg/ml bacitracin, and 0.5 mM PMSF [Tschopl et al., 1993]. Binding was terminated by filtration. Filters were washed twice by rapid filtration with 200 tdl volumes of 50 mM Tris-HCI pH 7.4/0.1% BSA at 2° C., and counted on an LKB gamma counter. Specific binding was analysed by non-linear regression using a single-site fitting function (Graphpad Prism). Non-specific binding was defined by binding in the presence of 1 $\mu$M competitor.

Peptide Synthesis and Purification

Peptide amides were synthesized by standard Boc or Fmoc solid-phase chemistry.

Boc synthesis was carried out using polystyrene based NBHA resin. Acetylation at the end of the synthesis was carried out using acetic anhydride in methanol. Peptides were cleaved by hydrogen fluoride containing phenol (1.3 g to 10 ml) as a scavenger and extracted into an aqueous phase (30% aqueous acetonitrile v/v). Scavengers were washed with ether and the crude aqueous extracts were then lyophilised to yield crude peptide. Side chain protection groups chosen for each amino acid were removed during the cleavage process. Peptides were purified by ion-exchange and reversed phase HPLC (high pressure liquid chromatography) to 95%.

Fmoc synthesis was carried using tentagel SRAM resin. Acetylation is performed as the last cycle using AcONSu (N-succinimidyl ester of acetic acid). Peptides were cleaved by 95% TFA containing thioanisole and p-cresol as scavengers and extracted into an aqueous phase containing 30% acetonitrile. Scavengers were washed with ether and the crude aqueous extracts were then lyophilised to yield crude peptides, which were purified by ion-exchange and reversed phase HPLC to 95%.Peptides were analysed for amino acid composition, and for correct molecular ion by electrospray mass spectrometry. Purity was estimated by both analytical HPLC and CE (capillary electrophoresis). All peptides carrying net positive charges were presented as acetate salts and peptide contents in all samples were determined based on the Pierce standard used in Picotag amino acid analysis.

Results and Discussion

Novel peptides, based on the amino acid sequence of neuropeptide Y in the region encompassed by amino acids 24–36, have been synthesized and tested for in vivo activity.

Of all the molecules tested in vivo in rats, only NPY raised blood pressure significantly in a dose-dependent manner. None of the other compounds significantly changed blood pressure at the doses tested. This is indicative of a lack of direct effect on neuropeptide Y receptors associated with increases in blood pressure, the Y1 receptor subtype.

Administration of all compounds listed in Table 1 dose-dependently inhibited the reduction in heart rate due to electrical stimulation of the vagus nerve. Notably, substitution of Ala at any position of 24 to 31 in Ac[Leu28,Leu31]NPY(24–36) resulted in enhanced potency (reduction in $EC_{50}$) as an inhibitor of the effect of vagal stimulation on heart rate. This inhibition of the effect of vagal stimulation indicates a reduction in release of acetylcholine from the parasympathetic innervation to the heart and has been attributed to stimulation of NPY Y2 receptors (Potter et al., 1994). Ala substitutions at positions 24 to 31 were all associated with high affinity for NPY Y2 receptors and low affinity for NPY Y1 receptors (Table 1). Unexpectedly, there was no direct correlation between in vivo activity in inhibiting vagal nerve mediated reductions in heart rate and affinity for Y2 receptors and this could indicate enhanced in vivo stability of some compounds. The enhancement of biological activity by Ala substitution in any one of 8 of 13 amino acid residues of Ac[L28,L31]NPY24–36 was unexpected. Even more surprising was the finding that multiple Ala substitutions to produce compounds such as Ac[A24,A27,L28,L31]NPY24–36, Ac[A26,A27,L28,L31]NPY24–36 and Ac[A24,26,27,30,31,L28]NPY24–36 also enhanced in vivo activity at Y2 receptors. The observation that 5 residues of

TABLE 1

Activities in vivo (change in pulse interval ($P_1$: activity at Y2-like receptors) and in blood pressure (BP: activity at Y1 receptors) in anaesthetised rats) and affinities for Y1 and Y2 receptors in vitro of a series of peptides.

| Compound | $EC_{50}$ $\Delta P_1$ % (nmole) | Increase in BP (rel to NPY) | $IC_{50}$ (nM) SMS-MSN (Y2) | $IC_{50}$ (nM) SK-N-MC (Y1) |
|---|---|---|---|---|
| NPY | | 1 | 0.66 | 10.96 |
| AcNPY$_{24-36}$ | 3.98 | 0† | 0.5 | |
| Ac[L$_{28}$,I$_{30}$]NPY$_{24-36}$ | 1.26 | 0† | | |
| Ac[A$_{24}$,L$_{28}$,L$_{31}$]NPY$_{24-36}$ | 0.46 | 0† | 19.25 | |
| Ac[A$_{25}$,L$_{28}$,L$_{31}$]NPY$_{24-36}$ | 1.58 | 0† | 2 | |
| Ac[A$_{26}$,L$_{28}$,L$_{31}$]NPY$_{24-36}$ | 1.26 | 0† | 63.1 | |
| Ac[A$_{27}$,L$_{28}$,L$_{31}$]NPY$_{24-36}$ | 0.52 | 0† | 0.13 | |
| Ac[A$_{28}$,L$_{31}$]NPY$_{24-36}$ | 2.75 | 0† | 12.59 | |
| Ac[L$_{28}$,A$_{29}$,L$_{31}$]NPY$_{24-36}$ | 1.48 | 0† | 0.05 | |
| Ac[L$_{28}$,A$_{30}$,L$_{31}$]NPY$_{24-36}$ | 0.39 | 0† | 6.31 | |
| Ac[L$_{28}$,A$_{31}$]NPY$_{24-36}$ | 0.78 | 0† | 0.06 | |
| Ac[L$_{28}$,L$_{31}$,A$_{32}$]NPY$_{24-36}$ | 6.46 | 0† | 2.51 | |
| Ac[A$_{24}$,A$_{27}$,L$_{28}$,L$_{31}$]NPY$_{24-36}$ | 0.89 | 0† | 0.03 | |
| Ac[A$_{24,26,27,30,31}$,L$_{28}$]NPY$_{24-36}$ | 0.56 | 0† | 3.16 | >1000 |
| Ac[A$_{25}$,R$_{28}$,L$_{31}$]NPY$_{24-36}$ | 1.95 | 0† | 0.1 | 691.83 |
| Ac[L$_{28}$,L$_{31}$]NPY$_{24-36}$ | 3.16 | 0† | 3.90 | >100 |
| Ac[A$_{26,27}$,L$_{28,31}$]NPY$_{24-36}$ | 1 | 0† | | |

†: No response to 10 nmole dose 13 could be replaced by Ala means that the comparatively extended side chains in these positions (24,26,27,30,31) are not essential to the maintenance of efficacy or affinity at NPY Y2 receptors. This is surprising as the replaced amino acid residues are diverse in structure and properties, two are aromatic (His, Tyr), one with a carboxyamide side chain and the rest having aliphatic side chains carrying 3 carbon atoms more than Ala. Furthermore the affinity of the multi-Ala substituted compounds at NPY Y2 receptors was similar to, or better than, that of Ac[L28,L31]NPY24–36, even though substitution of Leu24 or of His26 alone by Ala resulted in an apparent reduction in affinity. Such maintenance, or enhancement of activities could not be predicted. The multiple Ala containing compound Ac[A24,A27,L28,L31]NPY24–36 was assessed for its ability to inhibit the increase of renal vascular resistance elicited by renal nerve stimulation. A 40 nmol dose of this compound, that exerted no direct effect on the circulation (Table 1), almost completely inhibited the effect of nerve stimulation (FIG. 1) demonstrating an inhibition of transmitter release from the stimulated nerve. This compound exhibits a high affinity for NPY Y2 receptors, so although receptors mediating inhibition of transmitter release from renal nerves have not been identified they can be characterised as Y2-like.

The in vivo observations demonstrate that these compounds have general ability to inhibit neurotransmitter release from sympathetic and parasympathetic nerves and the agents would be expected to have activity in circumstances where inhibition of neurotransmission, of any type, was desirable. Examples of circumstances where inhibition of neurotransmission may be desirable are conditions such as nasal congestion, pulmonary congenstion and neurogenic inflammation.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Aakerlund, L., U. Gether, T. W. Schwartz, and O. Thastrup (1990), $Y_1$ receptors for neuropeptide Y are coupled to mobilization of intracellular calcium and inhibition of adenylate cyclase, FEBS Lett. 260, 73–78.

Baraniuk, J. N., Castellino, S., Lundgren, J. D., Goff, J., Mullol, J., Merida, M., Shelhamer, J. H. and Kaliner, M. A. (1990), Neuropeptide Y (NPY) in human nasal mucosa. J. Respir. Cell Mol. Biol. 3, 165–173;

Bard, J. A., Walker, M. W., Branchek, T. A. and Weinshank, R. L. (1995), J. Biol. Chem., 270, 26762–26765. Cloning and functional expression of Y4 subtype receptor for pancreatic polypeptide, neuropeptide Y, and peptide YY.

Dahlöff, C., P. Dahlöff and J. M. Lundberg (1985), Enhancement of blood pressure increase upon α-adrenoceptor activation and direct pressor effects in pithed rats, Eur. J. Pharmacol. 109, 289.

Edvinsson, L. (1988), The effects of neuropeptide Y on the circulation, ISI Atlas of Science: Pharmacoloy 2, 359.

Fuhlendorff, J., U. Gether, L. Aakerlund, N. Langeland-Johansen, H. Tøgerson, S.GF. Melberg, U. B. Olsen, O. Thastrup, and T. W. Schwartz (1990), [Leu$^{31}$, Pro$^{34}$] Neuropeptide Y: A specific $Y_1$ receptor agonist, Proc. Natl. Acad. Sci. 87, 182–186.

Gerald, C., Walker, M. W., Criscione, L., Gustafson, E. L., Batzi-Hartmann, C., Smith, K. E., Vaysse, P., Durkin, M. M., Laz. T. M., Linemeyer, D. L., Schaffhauser, A. O., Whitebread, S., Hofbauer, K. G., Taber, R. I., Branchek, T. A. and Weinshank, R. L. (1996). A receptor subtype involved in neuropeptide-Y-induced food intake. Nature, 382, 168–171.

Gerald, C., Walker, M. W., Vaysse, P. J.-J, He, C., Branchek, T. A. and Weinshank, R. L. (1995) J. Biol. Chem., 270, 26758–26761. Expression cloning and pharmacological characterisation of a human hippocampal neuropeptide Y/peptide YY Y2 receptor subtype.

Gregor, P., Millham, M. L., Feng, Y., DeCarr, L. B., McCaleb, M. L., and Cornfield, L. J. (1996). FEBS Lett., 381, 58–62. Cloning and characterisation of a novel receptor of pancreatic polypeptide, a member of the neuropeptide Y receptor family.

Grundemar, L., Grundstrom, N., Joahansson, I. G. M., Andersson, R. G. G. and Hakanson, R. (1990) Suppression by neuropeptide Y of capsaicin-sensitive sensory nerve-mediated contraction in guinea-pig airways. Br. J. Pharmacol., 99, 473–476.;

Grundemar, L., Wahlestedt, C. and Wang, Z. Y. (1993) Neuropeptide Y suppresses the neurogenic inflammatory response in the rabbit eye; mode of action. Regul. Pept., 43, 57–64.

Grunditz, T., Uddman, R. and Sundler, F. (1994) Origin and peptide content of nerve fibers in the nasal mucosa of rats. Anat. Embryol. 189, 327–337.

Hashim, M. A. and Tadepalli, A. S. (1995) Cutaneous vasomotor effects of neuropeptide Y. Neuropeptides, 29, 263–271.

Herzog, H., Y. J. Hort, H. J. Ball, G. Hayes, J. Shine, and L. A. Selbie (1992), Cloned human neuropeptide Y receptor couples to two different second messenger systems, Proc. Natl. Acad. Sci. U.S.A. 89, 5794–5798.

Lacroix, J. S., Ulman, L. G. and Potter, E. K. (1994) Modulation by neuropeptide Y of parasympathetic nerve-evoked nasal vasodilitation via Y2 prejunctional receptor. Br. J. Pharmacol., 113, 479–484.

Lundberg, J. M., Anggard, A., Theodorsson, Norheim E., Pernow., J. (1984) Guanethidine-sensitive release of neuropeptide Y-like immunoreactivity in the cat spleen by sympathetic nerve stimulation. Neuorsci. Lett., 52, 175–180.

Lundberg, J. M., Hensen, A., Larsson, O., Rudehill, A., Saria, A & Fredholm B. B., (1988). Neuropeptide Y receptor in pig spleen; binding characteristics, reduction of cAMP formation and calcium antagonist inhibition of vasoconstriction. Eur. J. Pharmacol. Vol. 45; 21–29

Pernow, J. & Lundberg, J. M. (1989a). Release and vasoconstrictor effects of neuropeptide Y in relation to nonadrenergic sympathetic control of renal blood flow in the pig. Acta Physiol Scand, 136, 507–517.

Pernow, J & Lundberg, J. M. (1989b). Modulation of nonadrenaline and polypeptide (NOY) release in the pig kidney in vivo: involvement of alpha 2, NPY and angiotensin II receptors. Naunyn-Schmiedeberg's Arch Pharmacol., 340, 379–385.

Potter, E. K. and M. J. D. McCloskey, (1992), [Leu$^{31}$, Leu$^{34}$] neuropeptide Y, a selective functional agonist at neuropeptide Y receptors in anaesthetised rats, Neurosci. Lett. 134, 183–186.

Potter, E. K., (1985), Prolonged non-adrenergic inhibition of cardiac vagal action following sympathetic stimulation: neuromodulation by neuropeptide Y Neurosci. Lett. 54, 117–121.

Potter, E. K. (1988), Neuropeptide Y as an autonomic neurotransmitter, Pharm. Ther., 37, 251–273.

Potter, E. K., Mitchell, L., McCloskey, M. J., Tseng, A., Goodman, A. E., Shine, J. and McCloskey, D. I. (1989) Pre-and postjunctional actions of neuropeptide Y and related peptides. Regul. Pept 25, 167–177.

Potter, E. K., J. Fuhlendorff and T. W. Schwartz (1991), [Pro$^{34}$] neuropeptide Y selectively identifies postjunctional-mediated actions of neuropeptide Y in vivo in rats and dogs, Eur. J. Pharmacol. 193, 15–19.

Potter, E. K., Barden, J. A., McClosky, J. D., Selbie, L. A., tseng, A., Herzog, H. and Shine, J. (1994), A novel neuropeptide Y analog, N-acetyl(Leu28,Leu31) neuropeptide Y-(24–36), with functional specificity for the presynaptic (Y2) receptor. Eur. J. Pharmacol. Mol. Pharmacol. Sect., 267, 253–262.

Revington, M. L., E. K. Potter and D. I. McCloskey, (1987), Effects of neuropeptide Y on the pressor responses to phenylephrine and to activation of the sympathetic nervous system in anaesthetised rats, Clin. Exp. Pharmacol. Physiol. 14, 703–710.

Rioux, F., H. Bachelard, J. C. Martel and S. St.-Piere, (1986), The vasoconstrictor effect of neuropeptide Y and related peptides in the guinea pig isolated heart, Peptides, 7, 27–31.

Schwartz, T. W., J. Fuhlendorff, H., Langeland, J. C. T ögerson, S. P. Sheikh, (1989), in Neuropeptide Y—XIV Nobel Symposium, ed: V. Mutt; T. Hökfelt, K. Fuxe and J. M. Lundberg, Raven, N.Y. pp143.

Scott, C. W. Gomes, B. C., Hubbs, S. J., Koenigbauer, H. C. (1995). A filtration-based assay to quantitate granulocyte-macrophage colony-stimulating factor binding. Anal. Biochem., 228, 150–154.

Sheikh, S. P., R. Hakanson and T. W. Schwartz, (1989), $Y_1$ and $Y_2$ receptors for neuropeptide Y, FEBS Lett. 245, 209–214.

Tatemoto, K., M. Carlquist and V. Mutt, (1982), Neuropeptide Y—A novel brain peptide with structural similarities to peptide YY and pancreatic polypeptide, Nature 296, 659–660.

Tschöpl, M., Miller, R. C., Pelton, J., Stoclet, J. C. and Bucher, B. (1993) Br. J. Pharmacol. 110, 1098–1104. Vasoconstrictor effects of various neuropeptide Y analogues on the rat tail artery in the presence of phenylephrine.

Wahlestedt, C., N. Yanaihara and R. Håkanson, (1986), Evidence for different pre- and post-junctional receptors for neuropeptide Y and related peptides, Regul. Pep. 13, 307–318.

Warner, M. R. and M. N. Levy, (1989), Neuropeptide Y as a putative modulator of the vagal effects on heart rate, Cir. Res. 64, 882–889.

What is claimed is:

1. A ligand for a neuropeptide Y receptor, neuropeptide Y Y2 receptor, and/or a neuropeptide Y Y2-like receptor selected from the group consisting of the following:

Ac-Ala-Arg-Ala-Ala-Leu-Asn-Ala-Ala-Thr-Arg-Gln-Arg-Tyr-NH$_2$ (SEQ ID NO: 1),

Ac-Ala-Arg-His-Tyr-Leu-Asn-Leu-Leu-Thr-Arg-Gln-Arg-Tyr-NH$_2$ (SEQ ID NO: 2),

Ac-Leu-Ala-His-Tyr-Leu-Asn-Leu-Leu-Thr-Arg-Gln-Arg-Tyr-NH$_2$ (SEQ ID NO: 3),

Ac-Leu-Arg-Ala-Tyr-Leu-Asn-Leu-Leu-Thr-Arg-Gln-Arg-Tyr-NH$_2$ (SEQ ID NO: 4),

Ac-Leu-Arg-His-Ala-Leu-Asn-Leu-Leu-Thr-Arg-Gln-Arg-Tyr-NH$_2$ (SEQ ID NO: 5),

Ac-Leu-Arg-His-Tyr-Ala-Asn-Leu-Leu-Thr-Arg-Gln-Arg-Tyr-NH$_2$ (SEQ ID NO: 6),

Ac-Leu-Arg-His-Tyr-Leu-Ala-Leu-Leu-Thr-Arg-Gln-Arg-Tyr-NH$_2$ (SEQ ID NO: 7),

Ac-Leu-Arg-His-Tyr-Leu-Asn-Ala-Leu-Thr-Arg-Gln-Arg-Tyr-NH$_2$ (SEQ ID NO: 8),

Ac-Leu-Arg-His-Tyr-Leu-Asn-Leu-Ala-Thr-Arg-Gln-Arg-Tyr-NH$_2$ (SEQ ID NO: 9),

Ac-Ala-Arg-His-Ala-Leu-Asn-Leu-Leu-Thr-Arg-Gln-Arg-Tyr-NH$_2$ (SEQ ID NO: 10), and Ac-Leu-Arg-Ala-Ala-Leu-Asn-Leu-Leu-Thr-Arg-Gln-Arg-Tyr-NH$_2$ (SEQ ID NO: I1) wherein Ac is acetyl.

2. A pharmaceutical composition comprising a ligand according to claim 1 and a pharmaceutical carrier.

3. A method of relieving nasal congestion, attenuating cardiac vagal action, treating vasoconstriction predisposing to acute renal failure, or treating hypertension in a subject wherein said method includes administering to the subject an effective amount of a composition according to claim 2.

4. A method according to claim 3 wherein the said composition is administered nasally.

* * * * *